US009400266B2

(12) United States Patent  (10) Patent No.: US 9,400,266 B2
Hale et al.  (45) Date of Patent: Jul. 26, 2016

(54) GAS CHROMATOGRAPH WITH IMPROVED OPERATION

(71) Applicant: Rosemount Analytical Inc., Houston, TX (US)

(72) Inventors: Shane Hale, Jersey Village, TX (US); Wanjun Yu, Sugarland, TX (US)

( * ) Notice: Subject to any disclaimer, the term of this patent is extended or adjusted under 35 U.S.C. 154(b) by 0 days.

(21) Appl. No.: 13/826,610

(22) Filed: Mar. 14, 2013

(65) Prior Publication Data

US 2014/0260539 A1  Sep. 18, 2014

(51) Int. Cl.
*G01N 30/28* (2006.01)
*G01N 30/86* (2006.01)
*G01N 30/88* (2006.01)

(52) U.S. Cl.
CPC ............ *G01N 30/28* (2013.01); *G01N 30/8665* (2013.01); *G01N 30/88* (2013.01); *G01N 2030/8804* (2013.01)

(58) Field of Classification Search
CPC .................................................... G01N 30/28
USPC ........................................................ 73/23.42
See application file for complete search history.

(56) References Cited

U.S. PATENT DOCUMENTS

| 3,607,073 A * | 9/1971 | Stamm ........................... 436/140 |
| 2006/0284075 A1 * | 12/2006 | Bonne et al. ................... 250/288 |
| 2008/0289397 A1 | 11/2008 | Hassan et al. | |

FOREIGN PATENT DOCUMENTS

JP  3707701 B2  10/2005

OTHER PUBLICATIONS

"Google search for ["peak area change" chemistry elution]", retrieved at <<https://www.google.com/webhp?sourceid=chrome-instant&ion=1&espv=2&ie=UTF-8#q=%22peak%20area%20change%22%20chemistry%20elution>>, retrieved on Mar. 4, 2015. 1 page.
"ABB NGC8200 Start-Up Guide, TotalFlow Measurement & Control Systems", © 2006 by ABB Inc., p. 1-23.
"Process Analytics throughout the entire natural gas pipeline supply chain", Case Study—Dec. 2008, Siemens AG, 13 pages.
"Danalyzer Gas Chromatograph Brochure", Emerson Process Management, © 2010 Daniel Measurement and Control, Inc., 8 pages.
First Office Action from Chinese counterpart Application No. 201310460101.2, dated Feb. 2, 2015, 9 pages.
Second Office Action from Chinese counterpart Application No. 201310460101.2, dated Sep. 6, 2015, 11 pages with English Translation.

\* cited by examiner

*Primary Examiner* — Daniel S Larkin
*Assistant Examiner* — Alex Devito
(74) *Attorney, Agent, or Firm* — Christopher R. Christenson; Kelly, Holt & Christenson, PLLC

(57) ABSTRACT

A gas chromatograph includes a sample inlet configured to receive a sample of interest and a carrier gas inlet configured to receive a carrier gas. A plurality of fluid flow valves are operably coupled to the sample inlet and the carrier gas inlet. A detector is operably coupled to the plurality of fluid flow valves and is configured to provide an analytic indication relative to the sample of interest. A controller is operably coupled to the plurality of fluid flow valves and is coupled to memory storing user-configurable information that is accessed by the controller to affect operation of the gas chromatograph.

8 Claims, 5 Drawing Sheets

GAS CHROMATOGRAPH WITH IMPROVED OPERATION

BACKGROUND

Gas chromatography is the separation of a mixture of chemical compounds due to their migration rates through a chromatograph column. This separates the compounds based on differences in boiling point, polarity, or molecular size. The separated compounds then flow across a suitable detector such as a thermal conductivity detector (TCD) that determines the concentration of each compound represented in the overall sample. Knowing the concentration of the individual compounds makes it possible to calculate certain physical properties such as BTU or specific gravity using industry-standard equations.

Modern gas chromatographs use multiple valves and columns to split the separation of components into several sub-processes in order to significantly speed up the analysis times and to improve the separation and isolation of individual components. The timing of the valve switching in a gas chromatograph is very important in order to ensure that the change in the analytical flow path occurs after all of one component has left a column, but before any of the next component has left the column. For example, with reference to FIG. 1, the valve timing should occur after component n-C5 has left the column, but before the next component, C6, begins to elute.

Over an extended period of operation (generally several months to years), contamination in the flow path and changes to the performance of the column can cause the time required for a component to exit the column (elution time) to change. Since the valve timing in a gas chromatograph is typically a fixed value, slowly one of the components will be gradually "cut" by the valve switching. When a component is cut by the valve switching, some of the cut component does not reach the detector when the gas chromatograph is configured to measure it and thus the measurement is incorrect. For example, FIGS. 2A and 2B illustrate a pair of examples where incorrect valve timing can generate errors. In the first example, FIG. 2A shows the valve timing occurring too late. In this example, some portions of C6 will be included in the detection of the previous peak (n-C5). In the second example, FIG. 2B shows valve timing occurring too early. In the second example, some portions of n-C5 are not fully eluted, and thus will not be detected by the detector of the gas chromatograph.

SUMMARY

A gas chromatograph includes a sample inlet configured to receive a sample of interest and a carrier gas inlet configured to receive a carrier gas. A plurality of fluid flow valves are operably coupled to the sample inlet and the carrier gas inlet. A detector is operably coupled to the plurality of fluid flow valves and is configured to provide an analytic indication relative to the sample of interest. A controller is operably coupled to the plurality of fluid flow valves and is coupled to memory storing user-configurable information that is accessed by the controller to affect operation of the gas chromatograph.

DETAILED DESCRIPTION OF ILLUSTRATIVE EMBODIMENTS

Figure 1:
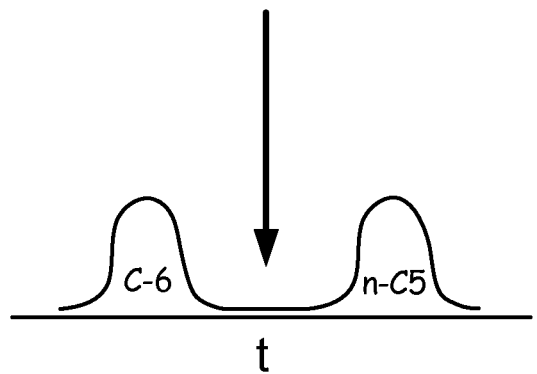
FIG. 1 is a diagrammatic chart showing proper valve timing in a gas chromatograph.
Figure 2A:
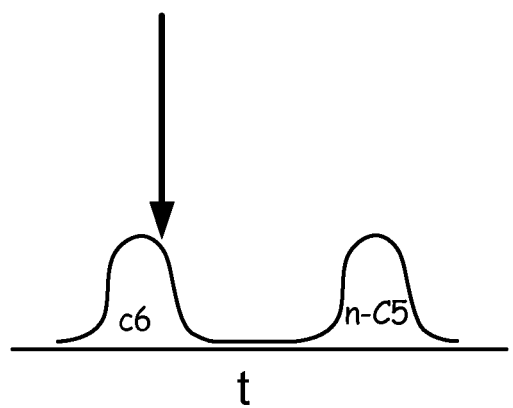
FIGS. 2A and 2B are diagrammatic charts showing improper valve timing in a gas chromatograph.
Figure 2B:
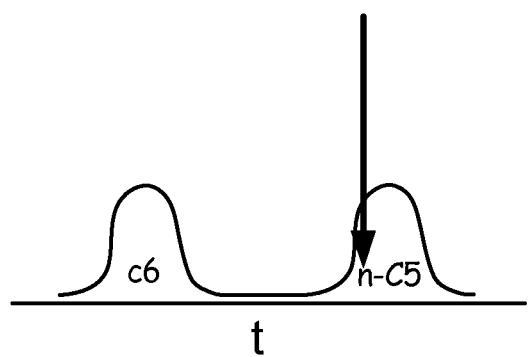
Figure 3:
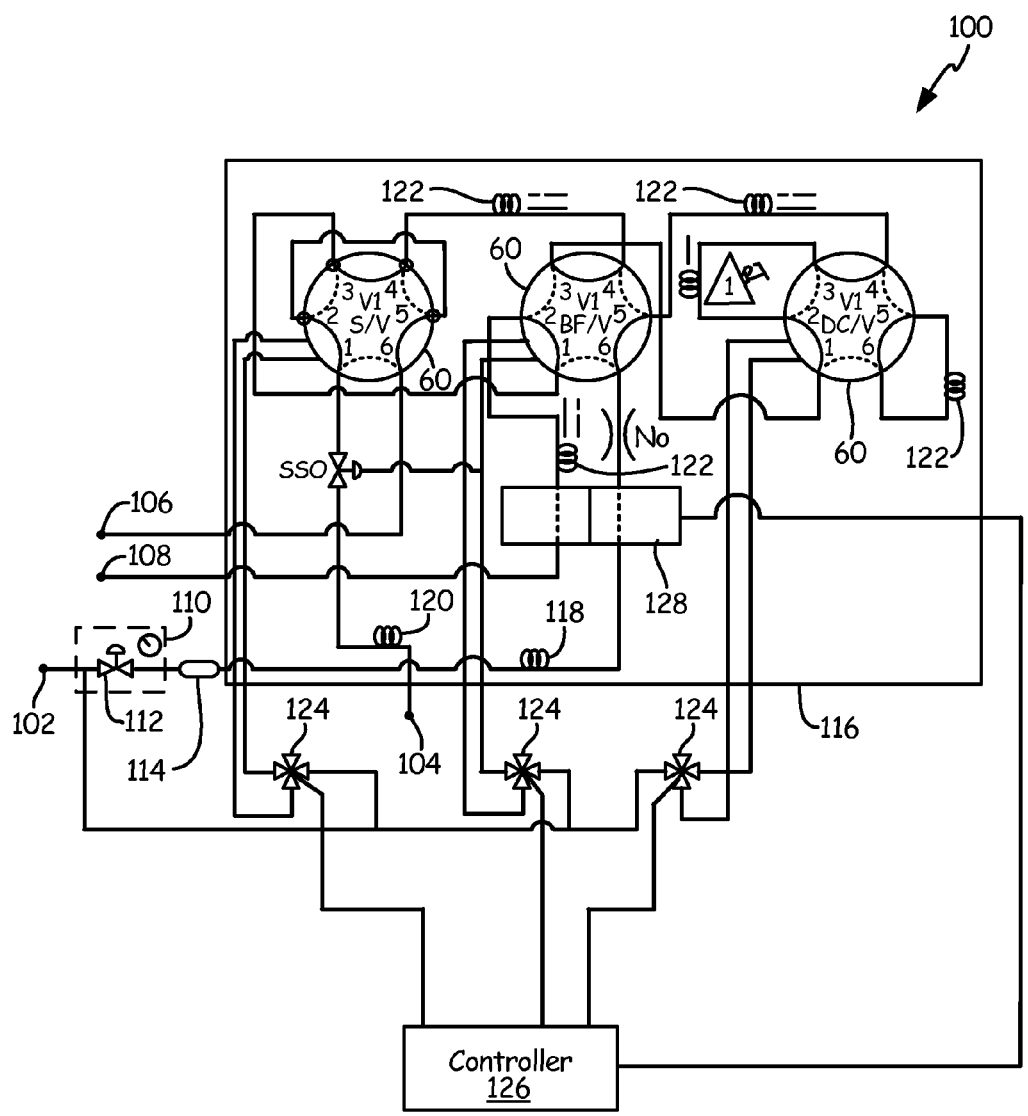
FIG. 3 is a diagrammatic system view of a gas chromatograph with which embodiments of the present invention are particularly useful.

FIG. 3 is a diagrammatic system view of a gas chromatograph with which embodiments of the present invention are particularly useful. Gas chromatograph 100 includes a carrier gas inlet 102, sample inlet 104, sample vent outlet 106 and measure vent outlet 108 for connecting to suitable sources of carrier gas, sample gas, and appropriate disposal lines. Carrier gas is provided to flow panel 110 where it passes through a regulator 112 and dryer 114 before entering analyzer oven 116 and passing through carrier gas pre-heater coil 118. Sample gas enters chromatograph 100 via sample inlet 104 and passes through sample gas pre-heater coil 120 within analyzer oven 116. Both sample gas and carrier gas eventually enter a plurality of pneumatically-controlled multiport selector valves 60 in order to selectably flow various volumes of sample and/or carrier gas through various chromatographic columns 122 in accordance with known gas chromatography techniques. Each of pneumatically-controlled multiport selector valves 60 is fluidically coupled to a respective solenoid 124 that receives its control signal from controller 126. As shown in FIG. 3, each pneumatically-controlled multiport selector valve 60 has a pair of states. In the first state, the fluidic connections of each valve 60 are shown in solid lines. The fluidic connections of each valve 60 in the second state are shown in phantom. Controller 126 is also operably coupled to detector 128, which is preferably a thermal conductivity detector disposed within analyzer oven 116. Thus, controller 126 is able to fully control flow through gas chromatograph 100 by virtue of controlling solenoids 124. Additionally, controller 126 is able to determine the response of detector 128 to gas flow therethrough. In this way, controller 126 is able to selectably introduce the sample into a chromatographic column for a selected amount of time; reverse the flow of gas through the chromatographic column; and direct the reversed flow through the detector to observe and/or record the detector response over time. This provides chromatographic analysis relative to the sample.

Controller 126 preferably includes a microprocessor or other suitable device that is able to execute a sequence of instructions; calculate analytic parameters; and store information. Controller 126 may include, or be coupled to, memory both volatile and non-volatile. In accordance with embodiments of the present invention, controller 126 is configured to receive and store a number of user-specified parameters that allow significant configuration and adaptation of the chromatograph for various applications.

Figure 4:
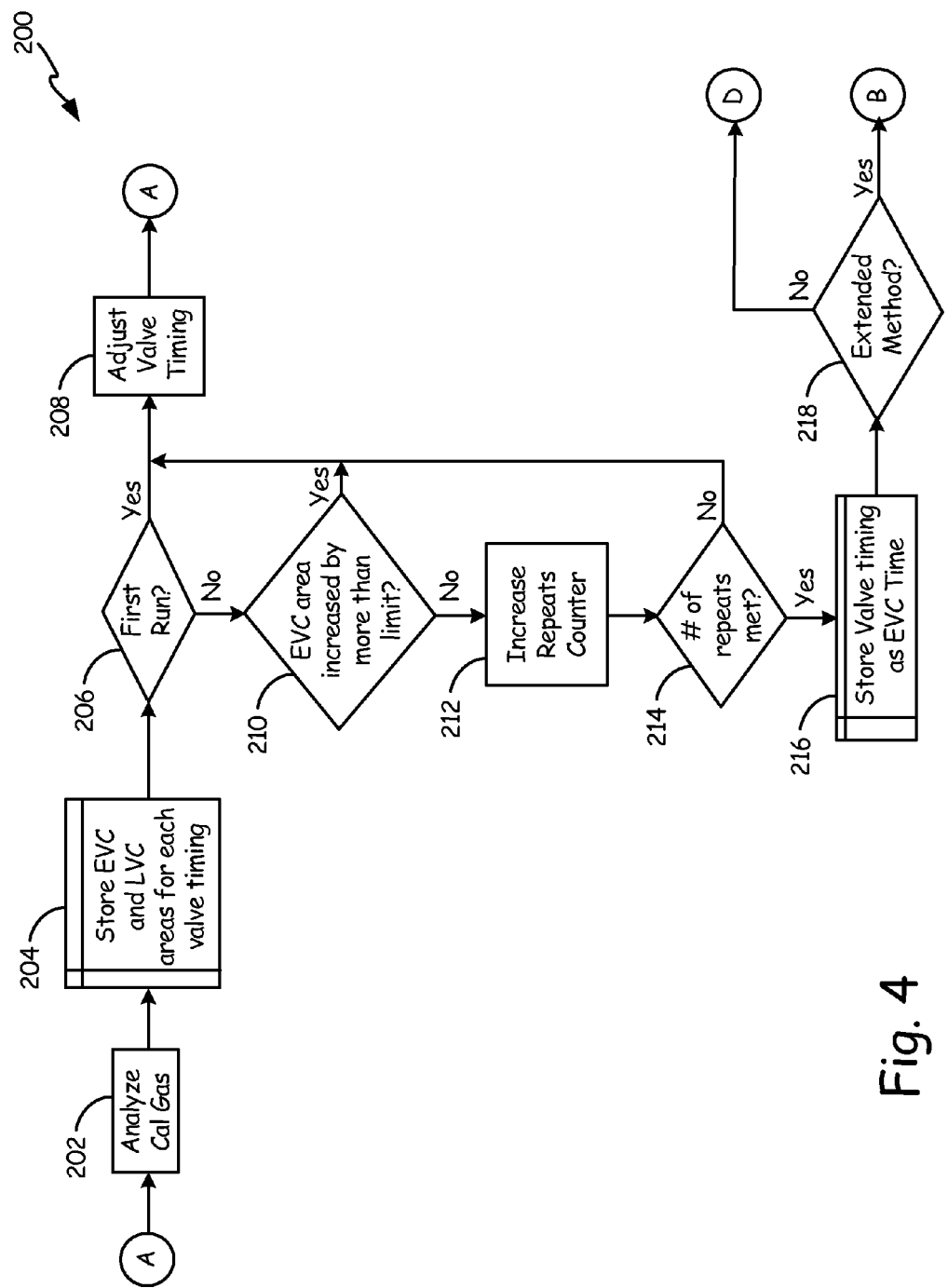
FIG. 4 is a flow diagram of a portion of a method of adjusting valve timing in a gas chromatograph in accordance with an embodiment of the present invention.

FIG. 4 is a flow diagram of a portion of a method of adjusting valve timing in a gas chromatograph in accordance with an embodiment of the present invention. One of the important features provided by embodiments of the present invention is a user-specified threshold for determining when to adjust valve timing of the gas chromatograph. Method 200 begins at node A where control passes to block 202 where a calibration gas is introduced to the gas chromatograph and analyzed. The calibration gas has known constituents in known proportions. Thus, an analysis of the calibration gas provides an indication relative to accuracy and efficacy of the gas chromatograph. For each valve timing event, one component is configured as the component cut by early valve timing (early valve-cut component, EVC) and one component is configured as the component cut by late valve timing (late-cut component, LVC). At block 204, the EVC and LVC are stored for each valve timing. Next, block 206 determines if method 200 is executing for the first time. If so, control passes to block 208 where the valve timing is adjusted and then the method repeats by returning to entry node A. If method 200 is not executing for the first time, control passes from block 206 to block 210. At block 210, if controller 126 determines that the EVC area has increased more than a user-specified limit or threshold, stored in controller 126, then control passes from block 210 to block 208 where the valve timing is automatically adjusted and the method is repeated by returning to node A. If, at block 210, however, the EVC area has not increased by more than the user-specified limit then control passes to block 212 where the number of iterations, or repeats, is increased by one. Control passes from block 212 to block 214 where the number of iterations is checked to see if an end condition is met. If the end condition is not met, control passes to block 208 where the valve timing is adjusted and the method repeats by returning to node A. On the other hand, if the end condition is satisfied, control passes from block 214 to block 216 where the valve timing is stored as the EVC time. Control then passes to block 218 where the method determines whether an extended method portion should be executed. If the extended method portion is not to be executed, then control passes to node D (See FIG. 6). If the extended method portion is to be executed, then control passes to node B which is described below with respect to FIG. 5.

Figure 5:
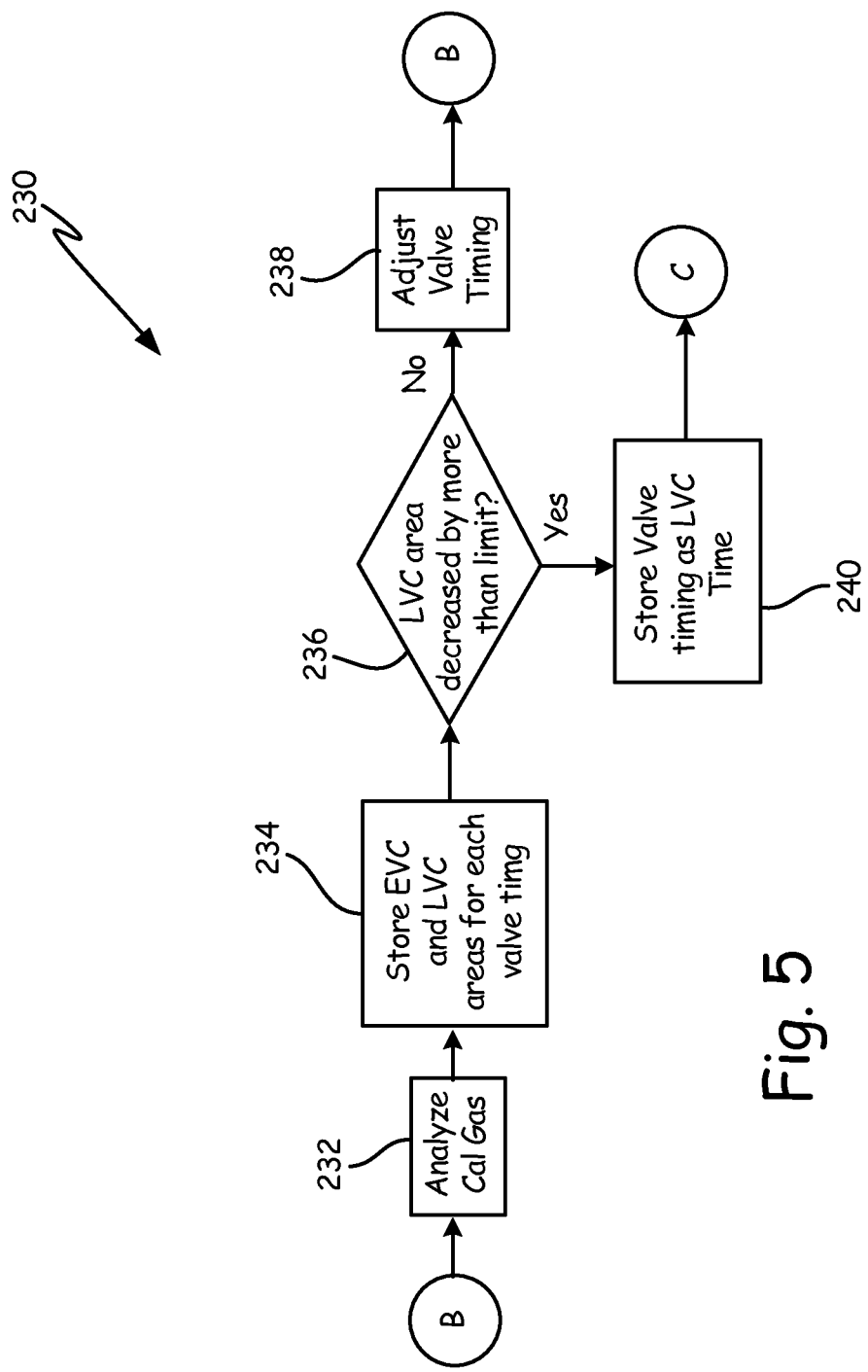
FIG. 5 is a flow diagram of a portion of a method of adjusting valve timing in a gas chromatograph in accordance with an embodiment of the present invention.

FIG. 5 is a flow diagram of a portion of a method of adjusting valve timing in a gas chromatograph in accordance with an embodiment of the present invention. FIG. 5 illustrates an extended portion of method 200 which can be selectively executed based on a determination by controller 126 during block 218 (shown in FIG. 4). Extended portion 230 begins at node B where control passes to block 232 where calibration gas is analyzed, just as in block 202. For each valve timing event, one component is configured as the component cut by early valve timing (early valve-cut component, EVC) and one component is configured as the component cut by late valve timing (late-cut component, LVC). At block 234, the EVC and LVC are stored for each valve timing. Control then passes to block 236 where controller 126 determines whether the LVC area has decreased more than a user-specified limit, stored in controller 126. If the LVC area has not decreased by more than the user-specified limit, then control passes to block 238 where the valve timing is adjusted and the portion of the method is repeated by returning to node B. However, if the LVC area has decreased by more than the user-specified limit, then control passes to block 240 where the valve timing is stored as the LVC time, and control is passed to node C (See FIG. 6).

Figure 6:
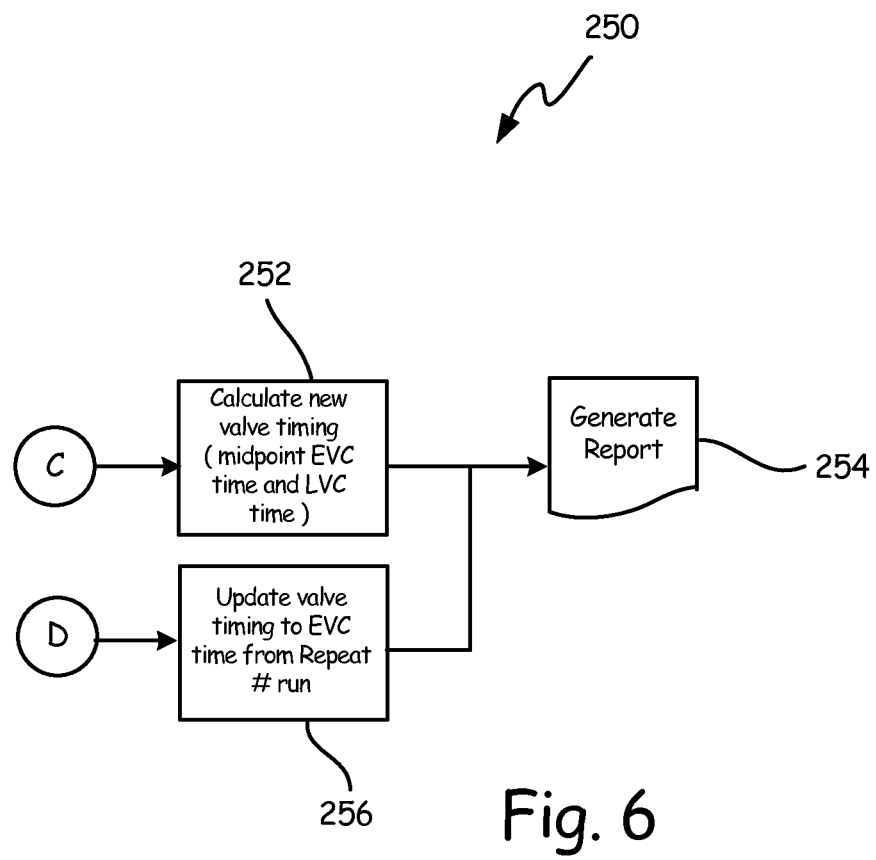
FIG. 6 is a flow diagram of a portion of a method of adjusting valve timing in a gas chromatograph in accordance with an embodiment of the present invention.

FIG. 6 is a flow diagram of a portion of a method of adjusting valve timing in a gas chromatograph in accordance with an embodiment of the present invention. Portion 250 has two entry points. One entry point, node C, is executed after the extended method portion described above with respect to FIG. 5. From node C, control passes to block 252 where controller 126 calculates new valve timing (midpoint EVC time and LVC time). Next, control passes to block 254 where a valve timing report is generated. The other entry point for method portion 250 is node D, which executes from block 218 (See FIG. 4) when the extended method portion 230 is not executed. From node D, control passes to block 256 where the valve timing is updated to the EVC time stored after completion of iteration of method 200. Control then passes from block 256 to block 254 where a valve timing report is generated.

Embodiments of the present invention generally include a programmable controller 126 that is preferably part of a replaceable analytical module of the gas chromatograph. From a user interface, or other suitable source, controller 126 is able to receive input from a user to configure or otherwise tune operation of the gas chromatograph. By independently adjusting both on-time events and off-time events for each individual valve in the gas chromatograph, controller 126 is able to provide a user with an array of available analytical methods that can be tailored to specific analysis and functions as desired by the user. As set forth above, one of the user-specified quantities is a threshold for an EVC area increase. Similarly, the user is also able to specify a threshold for an LVC area decrease. Further still, the user can specify a number of additional parameters. Specifically, the user can specify and controller 126 will store parameters related to timed event offsets. These offsets are preferably based on the retention time of a component. Another important user-specified parameter is the peak area change limits. The peak area change limits are used to determine valve timing adjustments and are configurable by the end user. Examples of quantities that may be specified by the user for peak area change limits include a 1% change, 2% change, or 5% change. Finally, the valve timing starting points and default values for the timed events are saved as parameters in or with controller 126. As set forth above, since the starting parameters used by controller 126 are stored in a component of a removable analytical module, these valve timing starting points travel with the valves to which they are directed. However, the valve timing starting points can also be accessed and/or changed by a user via the user interface or other suitable methods. Further, any suitable parameters can be user-specified to allow the gas chromatograph to be fully configurable by the end user.

Although the present invention has been described with reference to preferred embodiments, workers skilled in the art will recognize that changes may be made in form and detail without departing from the spirit and scope of the invention.

What is claimed is:

1. A gas chromatograph comprising:
a sample inlet configured to receive a sample of interest;
a carrier gas inlet configured to receive a carrier gas;
a plurality of fluid flow valves operably coupled to the sample inlet and the carrier gas inlet;
a detector operably coupled to the plurality of fluid flow valves and configured to provide an analytic indication relative to the sample of interest; and
a controller that is part of a removeable analytical module, wherein the controller is configured to operably coupled to the plurality of fluid flow valves, the controller being coupled to memory storing user-configurable parameters that are automatically accessed by the controller, wherein the controller automatically affects operation of the gas chromatograph by applying the stored user-configurable parameters to the operation of the gas chromatograph, wherein the user-configurable parameters comprise user-configurable valve information, and wherein the user-configurable valve information includes a peak area change limit.

2. The gas chromatograph of claim 1, wherein the user-configurable valve information also includes user-configurable valve timing information.

3. The gas chromatograph of claim 2, wherein the user-configurable valve information includes timed event offsets based on retention time.

4. The gas chromatograph of claim 1, wherein the peak area change limit is an early valve-cut component (EVC) increase threshold.

5. The gas chromatograph of claim 1, wherein the peak area change limit is a late valve-cut component (LVC) decrease threshold.

6. The gas chromatograph of claim 1, wherein the parameters include a plurality of valve timing starting values.

7. A method of automatically iteratively adjusting valve timing in a gas chromatograph, the method comprising:
   providing a calibration gas to the gas chromatograph having at least one valve;
   storing an early valve-cut component (EVC) area and a late valve-cut component area for each valve timing;
   adjusting valve timing if an early valve-cut component area has increased beyond a user-specified threshold; and
   triggering an iterative process for determining a new EVC time, the iterative process being conducted by a controller within the gas chromatograph, the iterative process comprising: increasing an iterator;
   comparing the iterator if the early valve-cut component area has not increased beyond a user-specified threshold;
   determining whether the iterator has reached an end condition and, if so, storing valve timing as a new EVC time, otherwise adjusting valve timing; and repeating the steps of increasing the iterator, comparing the iterator, and
   determining whether the iterator has reached an end condition, wherein the end condition is at least partially determined by a stored user-specified parameter; and using the new stored valve timing for subsequent chromatographic analysis.

8. The method of claim 7, and further comprising:
   determining if a late valve-cut component (LVC) area has decreased more than a user specified threshold, and if not, adjusting valve timing and repeating the step of determining if the late valve-cut component area has decreased more than the user-specified threshold and adjusting valve-timing, otherwise storing valve timing as LVC time.

* * * * *